US012642837B2

(12) United States Patent
Martinez-Hackert et al.

(10) Patent No.: US 12,642,837 B2
(45) Date of Patent: Jun. 2, 2026

(54) METHODS OF PREVENTING OR TREATING FATTY DEGENERATION OF SKELETAL MUSCLE

(71) Applicant: Board of Trustees of Michigan State University, East Lansing, MI (US)

(72) Inventors: Erik Martinez-Hackert, Okemos, MI (US); Monique Floer, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 872 days.

(21) Appl. No.: 17/628,495

(22) PCT Filed: Jul. 22, 2020

(86) PCT No.: PCT/US2020/043119
§ 371 (c)(1),
(2) Date: Jan. 19, 2022

(87) PCT Pub. No.: WO2021/021528
PCT Pub. Date: Feb. 4, 2021

(65) Prior Publication Data
US 2022/0362333 A1 Nov. 17, 2022

Related U.S. Application Data

(60) Provisional application No. 62/879,009, filed on Jul. 26, 2019.

(51) Int. Cl.
*A61K 38/17* (2006.01)
*A61P 21/06* (2006.01)

(52) U.S. Cl.
CPC ............ *A61K 38/179* (2013.01); *A61P 21/06* (2018.01)

(58) Field of Classification Search
None
See application file for complete search history.

(56) References Cited

U.S. PATENT DOCUMENTS

| | | | |
|---|---|---|---|
| 9,809,637 B2 | 11/2017 | Kumar et al. | |
| 9,884,900 B2 | 2/2018 | Kr20180035884 | |
| 2005/0203022 A1 | 9/2005 | Gotwals et al. | |
| 2013/0302335 A1* | 11/2013 | Beaton .................... | A61P 43/00 435/254.11 |
| 2016/0287664 A1 | 10/2016 | Yu et al. | |
| 2016/0298093 A1* | 10/2016 | Kumar .................... | C07K 14/71 |

FOREIGN PATENT DOCUMENTS

| | | | |
|---|---|---|---|
| JP | 2001515360 A | 9/2001 |
| JP | 2018531914 A | 11/2018 |
| KR | 20180035884 A | 4/2018 |
| WO | WO-1998048024 A1 | 10/1998 |
| WO | WO-2010092974 A1 | 8/2010 |

OTHER PUBLICATIONS

Gonzalez et al., PLoS One, 2017; 12(5): e0177649 (Year: 2017).*
Liu et al., Journal Hepatology, 2011; 55: 612-625 (Year: 2011).*
Bhattacharya et al., PLoS One 12(3): e0171355. https://doi.org/10.1371/journal.pone.0171355; 22 pages total (Year: 2017).*
Pucci et al., Current Opinion in Structural Biology 2022, 72: 161-168 (Year: 2022).*
Pak et al., PLoS One 18(3): e0282689. https://doi.org/10.1371/journal.pone.0282689 (Year: 2023).*
Office Action from corresponding Japanese Application No. 2022-505278 dated Mar. 14, 2023.
International Search Report from corresponding PCT Application No. PCT/US2020/043119 dated Nov. 20, 2020.
Written Opinion from corresponding PCT Application No. PCT/US2020/043119 dated Nov. 20, 2020.
Lemos, D.R., et al., (2015), "Nilotinib reduces muscle fibrosis in chronic muscle injury by promoting TNF-mediated apoptosis of fibro/adipogenic progenitors," Nature Medicine, 21(7): 786-794.
Loiselle, A.E., et al., (2015), "Development of Antisense Oligonucleotide (ASO) Technology Against Tgf-β Signaling to Prevent Scarring During Flexor Tendon Repair," J Orthop Res., 33(6): 859-866.
Muraoka, R.S., et al., (2002) "Blockade of TGF-β inhibits mammary tumor cell viability migration, and metastases," The Journal of Clinical Investigation, 109(12): 1551-1559.
Pagano, A.F., et al., (2019) "Muscle Resting and TGF-β Inhibitor Treatment Prevent Fatty Infiltration Following Skeletal Muscle Injury," Cellular Physiology and Biochemistry, 53: 62-75.
Davies, M.R., et al., (2016), "TGF-β Small Molecule Inhibitor SB431542 Reduces Rotator Cuff Muscle Fibrosis and Fatty Infiltration By Promoting Fibro/Adipogenic Progenitor Apoptosis," Plos One, 11(5): 1-15.
Gladstone, J. N., et al., (2007), "Fatty infiltration and atrophy of the rotator cuff do not improve after rotator cuff repair and correlate with poor functional outcome," Am J Sports Med, 35, 719-728.
Goutallier, D., et al., (2009), "Long-term functional and structural outcome in patients with intact repairs 1 year after open transosseous rotator cuff repair," J Shoulder Elbow Surg, 18, 521-528.
Hoffmeyer, P., et al., (1990), "Pathological changes in the triceps surae muscle after rupture of the Achilles tendon" Int Orthop, 14, 183-188.
Klatte-Schulz, F., et al., (2018), "Different Achilles Tendon Pathologies Show Distinct Histological and Molecular Characteristics," Int J Mol Sci, 19.
Heikkinen, J., et al., (2017), "Soleus Atrophy Is Common After the Nonsurgical Treatment of Acute Achilles Tendon Ruptures: A Randomized Clinical Trial Comparing Surgical and Nonsurgical Functional Treatments," Am J Sports Med, 45, 1395-1404.

(Continued)

*Primary Examiner* — Christina M Borgeest
(74) *Attorney, Agent, or Firm* — Harness, Dickey & Pierce, PLC

(57) ABSTRACT

Pharmaceutical compositions comprising a selective TGF-β inhibitor, such as a TGFβRII-Fc, are provided herein to prevent, reverse, reduce the occurrence of and/or treat fatty degeneration of skeletal muscle. Additionally, the selective TGF-β inhibitors may be used to inhibit fibro-adipogenic progenitor cell (FAP) differentiation into adipocytes.

22 Claims, 8 Drawing Sheets

Specification includes a Sequence Listing.

(56) References Cited

OTHER PUBLICATIONS

Teichtahl, A. J., et al., (2015), "Vastus medialis fat infiltration—a modifiable determinant of knee cartilage loss," *Osteoarthritis Cartilage*, 23, 2150-2157.

Zacharias, A., et al., (2016), "Hip abductor muscle volume in hip osteoarthritis and matched controls," *Osteoarthritis Cartilage*, 24, 1727-1735.

Snow, B. J., et al., (2012), "Evaluation of muscle size and fatty infiltration with MRI nine to eleven years following hamstring harvest for ACL reconstruction," *J Bone Joint Surg Am*, 94, 1274-1282.

Passias, P. G., et al., (2018), "Fatty Infiltration of Cervical Spine Extensor Musculature: Is there a Relationship With Cervical Sagittal Balance?," *Clin Spine Surg*, 31: 428-434.

Jun, H. S., et al., (2016), "The Effect of Lumbar Spinal Muscle on Spinal Sagittal Alignment: Evaluating Muscle Quantity and Quality," *Neurosurgery*, 79, 847-855.

Reinders, I., et al., (2016), "Muscle Quality and Myosteatosis: Novel Associations With Mortality Risk: The Age, Gene/Environment Susceptibility (AGES)—Reykjavik Study," *Am J Epidemiol*, 183, 53-60.

Hilton, T. N., et al., (2008), "Excessive adipose tissue infiltration in skeletal muscle in individuals with obesity, diabetes mellitus, and peripheral neuropathy: association with performance and function," *Phys Ther*, 88, 1336-1344.

Marcus, R. L., et al., (2010), "Skeletal muscle fat infiltration: impact of age, inactivity, and exercise," *J Nutr Health Aging*, 14, 362-366.

Maddocks, M., et al., (2014), "Skeletal muscle adiposity is associated with physical activity, exercise capacity and fibre shift in COPD," *Eur Respir J*, 44, 1188-1198.

Akazawa, N., et al., (2018), "Muscle mass and intramuscular fat of the quadriceps are related to muscle strength in non-ambulatory chronic stroke survivors: A cross-sectional study," *PLoS One*, 13, e0201789.

Marden, F. A., et al., (2005), "Compositional analysis of muscle in boys with Duchenne muscular dystrophy using MR imaging," *Skeletal Radiol*, 34, 140-148.

Goldstein, J. A., and McNally, E. M., (2010), "Mechanisms of muscle weakness in muscular dystrophy," *J Gen Physiol*, 136, 29-34.

Cox, F. M., et al., (2011), "Magnetic resonance imaging of skeletal muscles in sporadic inclusion body myositis," *Rheumatology (Oxford)*, 50, 1153-1161.

Simon, N. G., et al., (2016), "Skeletal muscle imaging in neuromuscular disease," *J Clin Neurosci*, 33, 1-10.

Tresoldi, I., et al., (2013), "Tendon's ultrastructure," *Muscles Ligaments Tendons J*, 3, 2-6.

Yung, L. M., et al., (2016), "A Selective Transforming Growth Factor-beta Ligand Trap Attenuates Pulmonary Hypertension," *Am J Respir Crit Care Med*, 194, 1140-1151.

Aykul, S., and Martinez-Hackert, E., (2016), "Transforming Growth Factor-beta Family Ligands Can Function as Antagonists by Competing for Type II Receptor Binding," *The Journal of biological chemistry*, 291, 10792-10804.

Millan, F. A., et al., (1991), "Embryonic gene expression patterns of TGF beta 1, beta 2 and beta 3 suggest different developmental functions in vivo," *Development*, 111, 131-143.

Pelton, R. W., et al., (1991), "Immunohistochemical localization of TGF beta 1, TGF beta 2, and TGF beta 3 in the mouse embryo: expression patterns suggest multiple roles during embryonic development," *The Journal of cell biology*, 115, 1091-1105.

Hawinkels, L. J., and Ten Dijke, P., (2011), "Exploring anti-TGF-beta therapies in cancer and fibrosis," Growth Factors, 29, 140-152.

Ignotz, R. A., and Massague, J., (1985), "Type beta transforming growth factor controls the adipogenic differentiation of 3T3 fibroblasts," *Proceedings of the National Academy of Sciences of the United States of America*, 82, 8530-8534.

Havis, E., et al., (2016), "TGFbeta and FGF promote tendon progenitor fate and act downstream of muscle contraction to regulate tendon differentiation during chick limb development," *Development*, 143, 3839-3851.

Havis, E., et al., (2014), "Transcriptomic analysis of mouse limb tendon cells during development," *Development*, 141, 3683-3696.

Pryce, B. A., et al., (2009), "Recruitment and maintenance of tendon progenitors by TGFbeta signaling are essential for tendon formation," *Development*, 136, 1351-1361.

Liu, H., et al., (2015), "Mohawk promotes the tenogenesis of mesenchymal stem cells through activation of the TGFbeta signaling pathway," *Stem Cells*, 33, 443-455.

Vincenti, F., et al., (2017), "A Phase 2, Double-Blind, Placebo-Controlled, Randomized Study of Fresolimumab in Patients With Steroid-Resistant Primary Focal Segmental Glomerulosclerosis," *Kidney Int Rep*, 2, 800-810.

Formenti, S. C., et al., (2018), "Focal Irradiation and Systemic TGFbeta Blockade in Metastatic Breast Cancer," *Clin Cancer Res*, 24, 2493-2504.

Inman, G. J., et al., (2002), "SB-431542 is a potent and specific inhibitor of transforming growth factor-beta superfamily type I activin receptor-like kinase (ALK) receptors ALK4, ALK5, and ALK7," *Mol Pharmacol*, 62, 65-74.

Davies, M. R., et al., (2016), "TGF-beta Small Molecule Inhibitor SB431542 Reduces Rotator Cuff Muscle Fibrosis and Fatty Infiltration By Promoting Fibro/Adipogenic Progenitor Apoptosis," *PLoS One*, 11, e0155486.

Yingling, J. M., et al., (2018), "Preclinical assessment of galunisertib (LY2157299 monohydrate), a first-in-class transforming growth factor-beta receptor type I inhibitor," *Oncotarget*, 9, 6659-6677.

Aykul, S., et al., (2021) "Smad2/3 Activation Regulates Smad1/5/8 Signaling via a Negative Feedback Loop to Inhibit 3T3-L1 Adipogenesis," Int. J. Mol. Sci., 22: 1-21.

Aykul, S., et al., (2020) "TGF-B Family Inhibitors Blunt Adipogenesis via Non-Canonical Regulation of Smad Pathways," bioRxiv, p. 1-4.

Office Action from Chinese Application No. 202080053476.5 dated Jan. 12, 2024.

Extended European Search Report from corresponding EP Application No. 20847042.7 dated Mar. 28, 2023.

Kaji, D.A., et al., "Tgfβ signaling is required for tenocyte recruitment and functional neonatal tendon regeneration," eLife, p. 1-19 (2020).

Stepien, D.M., et al., "Tuning Macrophage Phenotype to Mitigate Skeletal Muscle Fibrosis," Journal of Immunology, 204(8): 2203-2215 (2020).

Haque, S. and Morris, J.C., "Transforming growth factor-β: A Therapeutic target for cancer," Human Vaccines & Immunotherapeutics, 13(8): 1741-1750 (2017).

Accornero, F., et al., "Myofiber-specific inhibition of TGFβ signaling protects skeletal muscle from injury and dystrophic disease in mice," Human Molecular Genetics, 23(25): 6903-6915 (2014).

Clouthier, D. E., et al. (1997). Hepatic fibrosis, glomerulosclerosis, and a lipodystrophy-like syndrome in PEPCK-TGF-beta1 transgenic mice. The Journal of clinical investigation, 100(11): 2697-2713.

Wankhade, U. D., et al. (2018). TGF-β receptor 1 regulates progenitors that promote browning of white fat. Molecular metabolism, 16: 160-171.

Lu, H., et al. (2013). Regulation of adipocyte differentiation and gene expression-crosstalk between TGFβ and wnt signaling pathways. Molecular biology reports, 40(9): 5237-5245.

Babaei, R., L., et al. (2018). Jak-TGFβ cross-talk links transient adipose tissue inflammation to beige adipogenesis. Science signaling, 11(527).

Peng, J., et al. (2015). Bone-Conditioned Medium Inhibits Osteogenic and Adipogenic Differentiation of Mesenchymal Cells In Vitro. Clinical implant dentistry and related research, 17(5): 938-949.

Kim, C. Y., et al. (2012). Selenate inhibits adipogenesis through induction of transforming growth factor-β1 (TGF-β1) signaling. Biochemical and biophysical research communications, 426(4): 551-557.

Li, R., et al. (2015). Mechanical stretch inhibits mesenchymal stem cell adipogenic differentiation through TGFβ1/Smad2 signaling. Journal of biomechanics, 48(13): 3665-3671.

(56)　　　　　　References Cited

OTHER PUBLICATIONS

Gruber, R., et al. (2013). Enamel matrix derivative inhibits adipocyte differentiation of 3T3-L1 cells via activation of TGF-βRI kinase activity. PloS one, 8(8): e71046.

Luo, H., et al. (2019). Growth differentiation factor 11 inhibits adipogenic differentiation by activating TGF-beta/Smad signalling pathway. Cell proliferation, 52(4): e12631.

R.A. Ignotz, & J. Massagué (1985). Type beta transforming growth factor controls the adipogenic differentiation of 3T3 fibroblasts., Proc. Natl. Acad. Sci. U.S.A. 82 (24): 8530-8534.

Aykul, S., et al. (2021). Smad2/3 Activation Regulates Smad1/5/8 Signaling via a Negative Feedback Loop to Inhibit 3T3-L1 Adipogenesis. International journal of molecular sciences, 22(16): 8472.

Choy, L., et al. (2000). Roles of autocrine TGF-beta receptor and Smad signaling in adipocyte differentiation. The Journal of cell biology, 149(3): 667-682.

* cited by examiner

SEQ ID NO: 4

Native Leader Sequence                    Splice insertion (25 a.a.)

```
                    1     10    20        30                                    35
Native TGFβRII short  MGRGLLRGLWPLHIVLWTRIAS TIPPHVQKS------------------------VNNDMIV . . .

1     10    20        30      40        50        60
Native TGFβRII long   MGRGLLRGLWPLHIVLWTRIAS TIPPHVQKSDVEMEAQKDEIICPSCNRTAHPLRHINNDMIV . . .
```

SEQ ID NO: 5

Fig. 1A

SEQ ID NO: 1

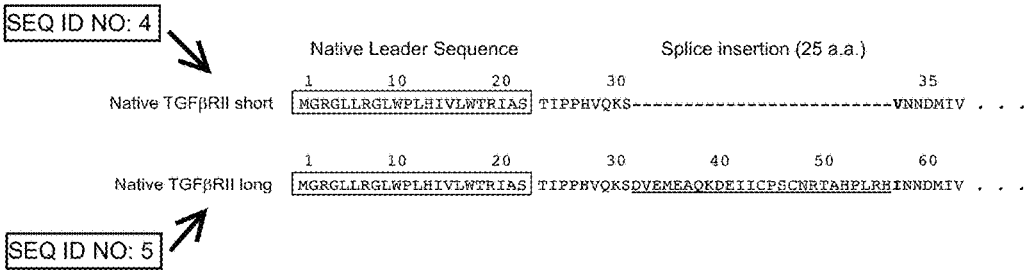

```
Uniprot SEQ D2JYI1   MGRGLLRGLWPLHIVLWTRIASTIPPHVQKSDVEMEAQKDEIICPSCNRTAHPLRHINND   60
Uniprot SEQ P37173   MGRGLLRGLWPLHIVLWTRIASTIPPHVQKS-----------------------VNND    35
                     ******************************                       :***
```

SEQ ID NO: 2

```
Uniprot SEQ D2JYI1   MIVTDNNGAVKFPQLCKFCDVRFSTCDNQKSCMSNCSITSICEKPQEVCVAVWRKNDENI  120
Uniprot SEQ P37173   MIVTDNNGAVKFPQLCKFCDVRFSTCDNQKSCMSNCSITSICEKPQEVCVAVWRKNDENI   95
                     ***********************************************************
```

```
Uniprot SEQ D2JYI1   TLETVCHDPKLPYHDFILEDAASPKCIMKEKKKPGETFFMCSCSSDECNDNIIFSEEYNT  180
Uniprot SEQ P37173   TLETVCHDPKLPYHDFILEDAASPKCIMKEKKKPGETFFMCSCSSDECNDNIIFSEEYNT  155
                     ***********************************************************
```

```
Uniprot SEQ D2JYI1   SNPDLLLVIFQV    192
Uniprot SEQ P37173   SNPDLLLVIFQV    167
                     ************
```

Fig. 1B

```
Lys Pro Lys Asp Thr Leu Met Ile Ser Arg Thr Pro Glu Val Thr Cys
    210             215             220

Val Val Val Asp Val Ser His Glu Asp Pro Glu Val Lys Phe Asn Trp
225             230             235                 240

Tyr Val Asp Gly Val Glu Val His Asn Ala Lys Thr Lys Pro Arg Glu
                245             250                 255

Glu Gln Tyr Asn Ser Thr Tyr Arg Val Val Ser Val Leu Thr Val Leu
            260             265             270

His Gln Asp Trp Leu Asn Gly Lys Glu Tyr Lys Cys Lys Val Ser Asn
            275             280             285

Lys Ala Leu Pro Ala Pro Ile Glu Lys Thr Ile Ser Lys Ala Lys Gly
    290             295             300

Gln Pro Arg Glu Pro Gln Val Tyr Thr Leu Pro Pro Ser Arg Asp Glu
305             310             315             320

Leu Thr Lys Asn Gln Val Ser Leu Thr Cys Leu Val Lys Gly Phe Tyr
            325             330             335

Pro Ser Asp Ile Ala Val Glu Trp Glu Ser Asn Gly Gln Pro Glu Asn
            340             345             350

Asn Tyr Lys Thr Thr Pro Pro Val Leu Asp Ser Asp Gly Ser Phe Phe
            355             360             365

Leu Tyr Ser Lys Leu Thr Val Asp Lys Ser Arg Trp Gln Gln Gly Asn
    370             375             380

Val Phe Ser Cys Ser Val Met His Glu Ala Leu His Asn His Tyr Thr
385             390             395                 400

Gln Lys Ser Leu Ser Leu Ser Pro Gly Lys
```

Fig. 1C (CONT.)

Muscle atrophy

*Cidec*

*Lep*

SEQUENCE LISTING

```
<160> NUMBER OF SEQ ID NOS: 5

<210> SEQ ID NO 1
<211> LENGTH: 167
<212> TYPE: PRT
<213> ORGANISM: Homo Sapiens

<400> SEQUENCE: 1

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val
                165
```

```
<210> SEQ ID NO 2
<211> LENGTH: 192
<212> TYPE: PRT
<213> ORGANISM: Homo sapiens

<400> SEQUENCE: 2

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
        130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

<210> SEQ ID NO 3
<211> LENGTH: 410
<212> TYPE: PRT
<213> ORGANISM: Artificial sequence
<220> FEATURE:
<223> OTHER INFORMATION: Full TGFbRII-Fc sequence

<400> SEQUENCE: 3

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
```

```
           130                    135                    140

Asp Asn Ile Ile Phe Ser Glu Glu Tyr Asn Thr Ser Asn Pro Asp Glu
145                    150                    155                    160

Gly Gly Gly Gly Gly Gly Gly Ser Gly Gly Gly Gly Ser Gly Gly Gly
                       165                    170                    175

Gly Ser Gly Asp Lys Ser Ser Asp Lys Thr His Thr Cys Pro Pro Cys
                180                    185                    190

Pro Ala Pro Glu Leu Leu Gly Gly Pro Ser Val Phe Leu Phe Pro Pro
            195                    200                    205

Lys Pro Lys Asp Thr Leu Met Ile Ser Arg Thr Pro Glu Val Thr Cys
        210                    215                    220

Val Val Val Asp Val Ser His Glu Asp Pro Glu Val Lys Phe Asn Trp
225                    230                    235                    240

Tyr Val Asp Gly Val Glu Val His Asn Ala Lys Thr Lys Pro Arg Glu
                245                    250                    255

Glu Gln Tyr Asn Ser Thr Tyr Arg Val Val Ser Val Leu Thr Val Leu
                260                    265                    270

His Gln Asp Trp Leu Asn Gly Lys Glu Tyr Lys Cys Lys Val Ser Asn
            275                    280                    285

Lys Ala Leu Pro Ala Pro Ile Glu Lys Thr Ile Ser Lys Ala Lys Gly
        290                    295                    300

Gln Pro Arg Glu Pro Gln Val Tyr Thr Leu Pro Pro Ser Arg Asp Glu
305                    310                    315                    320

Leu Thr Lys Asn Gln Val Ser Leu Thr Cys Leu Val Lys Gly Phe Tyr
                325                    330                    335

Pro Ser Asp Ile Ala Val Glu Trp Glu Ser Asn Gly Gln Pro Glu Asn
                340                    345                    350

Asn Tyr Lys Thr Thr Pro Pro Val Leu Asp Ser Asp Gly Ser Phe Phe
            355                    360                    365

Leu Tyr Ser Lys Leu Thr Val Asp Lys Ser Arg Trp Gln Gln Gly Asn
        370                    375                    380

Val Phe Ser Cys Ser Val Met His Glu Ala Leu His Asn His Tyr Thr
385                    390                    395                    400

Gln Lys Ser Leu Ser Leu Ser Pro Gly Lys
                405                    410
```

```
<210> SEQ ID NO 4
<211> LENGTH: 38
<212> TYPE: PRT
<213> ORGANISM: Homo sapiens

<400> SEQUENCE: 4

Met Gly Arg Gly Leu Leu Arg Gly Leu Trp Pro Leu His Ile Val Leu
1                   5                    10                    15

Trp Thr Arg Ile Ala Ser Thr Ile Pro Pro His Val Gln Lys Ser Val
                20                    25                    30

Asn Asn Asp Met Ile Val
            35
```

```
<210> SEQ ID NO 5
<211> LENGTH: 63
<212> TYPE: PRT
<213> ORGANISM: Homo sapiens

<400> SEQUENCE: 5

Met Gly Arg Gly Leu Leu Arg Gly Leu Trp Pro Leu His Ile Val Leu
```

-continued

```
1            5              10             15

Trp Thr Arg Ile Ala Ser Thr Ile Pro Pro His Val Gln Lys Ser Asp
            20              25             30

Val Glu Met Glu Ala Gln Lys Asp Glu Ile Ile Cys Pro Ser Cys Asn
        35              40             45

Arg Thr Ala His Pro Leu Arg His Ile Asn Asn Asp Met Ile Val
    50              55             60
```

METHODS OF PREVENTING OR TREATING FATTY DEGENERATION OF SKELETAL MUSCLE

CROSS-REFERENCE TO RELATED APPLICATIONS

This application claims the benefit under 35 U.S.C. § 119(e) of U.S. Provisional Patent Application No. 62/879,009 filed on Jul. 26, 2019. The contents of U.S. 62/879,009 is hereby incorporated by reference in its entirety.

U.S. GOVERNMENT RIGHTS

This invention was made with government support under GM121499 awarded by the National Institutes of Health. The government has certain rights in the invention.

REFERENCE TO AN ELECTRONIC SEQUENCE LISTING

This application contains references to amino acid sequences and/or nucleic acid sequences which have been submitted concurrently herewith as the sequence listing.txt file entitled "6550-000361-US-NPB_14_Jan_ 2025_ST25.txt", file size 8,225 Bytes (B), created on 14 Jan. 2025. The aforementioned sequence listing is hereby incorporated by reference in its entirety.

FIELD

The present invention generally relates to selective TGF-β inhibitors, pharmaceutical compositions thereof, and uses thereof, such as preventing and/or treating fatty degeneration of skeletal muscle.

BACKGROUND

The background description includes information that may be useful in understanding the present disclosure. It is not an admission that any of the information provided herein is prior art or relevant to the presently claimed invention, or that any publication specifically or implicitly referenced is prior art.

The transforming growth factor beta (TGF-β) family is a well-known family of structurally related proteins that control proliferation, differentiation, development regulation and other functions in many cell types. The TGF-β family includes canonical TGF-β, which forms a group of three isoforms, TGF-β1, TGF-β2, and TGF-β3. The three isoforms, TGF-β1-3, have long been known to have distinct functions. They are differentially expressed in various tissues and at distinct times during development.

Fatty degeneration ("FD") of muscle tissue can occur following injuries, repair surgeries, such as rotator cuff ("RC") repair surgery, and other conditions. Various approaches have been taken to attempt to inhibit TGF-β signaling, such as monoclonal antibodies and small molecules. Notably, targeting TGF-β pathways with a small molecule inhibitor (SB431542) in a mouse model of massive RC tears was reported to reduce FD of relevant muscles. However, SB431542 will not work clinically due to its broad specificity and poor pharmacological properties.

Additionally, fusion proteins comprising the TGF-β type II receptor linked to a portion of an immunoglobulin constant region ("TGFβRII-Fc") are reported in published International Patent Application, WO 1998/048024 and U.S. Pat. No. 9,809,637.

Thus, even though various selective TGF-β inhibitors are known in the art, there are currently no treatments that prevent or mitigate FD of muscles in humans. Therefore, a need exists to provide improved compositions and methods to prevent and/or treat FD.

SUMMARY

Various compositions and methods that employ a selective TGF-β inhibitor for preventing, reversing, reducing the occurrence of and/or treating FD in skeletal muscle are described herein comprising administering a therapeutically effective amount of a selective TGF-β inhibitor to a subject in need thereof.

In particular embodiments, the selective TGF-β inhibitor is administered to a subject before, during or after surgery, such as RC repair surgery.

In further embodiments, a method of inhibiting differentiation of fibro-adipogenic progenitor cells (FAPs) into adipocytes is also described herein. The method comprises contacting the intercellular compartment surrounding a FAP cell with an effective amount of a selective TGF-β inhibitor.

In particular embodiments, the selective TGF-β inhibitor is a TGFβRII-Fc as described herein.

In further particular embodiments, the selective TGF-β inhibitor is a TGFβRII-Fc from an animal species that is used to prevent, reverse, reduce the occurrence of and/or treat FD in the same animal species.

Various objects, features, aspects, and advantages will become more apparent from the following detailed description of preferred embodiments, along with the accompanying drawing in which like numerals represent like components.

BRIEF DESCRIPTION OF THE DRAWINGS

FIGS. 1A-1B show the two splice forms of TGFβRII that occur in nature, the native short-form and the native long-form. FIG. 1A shows that the long-form has an insertion of 25 amino acids after amino acid 31, and the amino acid following this insertion is changed from Val to Ile (shown in bold). FIG. 1B shows the sequences of the extracellular domains (ECDs) of both forms of TGFβRII. Uniprot SEQ P37173 (SEQ ID NO:1 herein) is the short-form; Uniprot SEQ D2JYI1 (SEQ ID NO:2 herein) is the long-form.

FIG. 3A is a schematic showing how fibro-adipogenic progenitor cells (FAPs) differentiate into adipocytes. See Aykul, S., Maust, J., Floer, M. and Martinez-Hackert, M. *TGF-B Family Inhibitors Blunt Adipogenesis Via Non-Canonical Regulation Of SMAD Pathways.* bioRxiv. Posted online on Mar. 14, 2020, which is hereby incorporated by reference in its entirety. FIGS. 3B-3G shows immunofluorescence analysis of 3T3-L1 cells that were grown in adipocyte differentiation medium for 8 days, with vehicle control (PBS) or 300 nM TGFβRII-Fc. FIG. 3B shows an image of cells that were stained for lipids with Nile-red (green); nuclei were stained with DAPI (magenta). FIG. 3C shows the quantification of the number of liqid droplets, FIG. 3D shows the average size of liqid droplets, FIG. 3E shows the average lipid area, FIG. 3F shows the normalized Nile-red fluorescence and FIG. 3G shows lipolysis activity. Hatched bars show vehicle control and white bars show TGFβRII-Fc treated cells. FIGS. 3H-3M show gene expression analysis of 3T3-L1 cells grown for different lengths of time in differentiation medium. Induction of adipocyte marker gene expression was analyzed by qRT-PCR on day 0, day 3 and day 8 in vehicle control (hatched bars) and TGFβRII-Fc treated cells (white bars). Data is shown, as fold induction after normalization to Rpl4, for Adipoq in FIG. 3H, for Cidec in FIG. 3I, for Fabp4 in FIG. 3J, for Lep in FIG. 3K, for Plin1 in FIG. 3L, and for Pparg in FIG. 3M. Significance was determined by two-way ANOVA and Sidaki's or Dunnett's multiple comparisons tests. (*p<0.05; p<0.01; *p<0.001; ****p<0.0001).

FIG. 4A shows pictures of muscles that were sectioned and stained with hematoxylin (blue) followed by Oil Red 0 (ORO). ORO detects intramuscular fat due to lipid droplets that form inside muscle fibers as well as intermuscular fat, which is a result of adipocytes growing in between muscle fibers (FI). FIG. 4B shows the quantification of total fat, FIG. 4C shows quantification of intermuscular fat, and FIG. 4D shows quantification of intramuscular fat from the quadriceps of mice (n=3). FIG. 4E-4J show gene expression analysis of quadriceps muscles. Gene expression was analyzed by qRT-PCR and normalized to the Rpl4 household gene. Data is shown as fold expression over chow fed mice for the fat cell marker genes Adipoq in FIG. 4E, for Cidec in FIG. 4F, for Fabp4 in FIG. 4G, for Lep in FIG. 4H, for Plin1 in FIG. 4I, and for Pparg in FIG. 4J. Significance was determined by one-way ANOVA followed by post-hoc Tukey's tests. (*p<0.05; **p<0.01)

FIG. 5A shows quantification of the loss in weight wet of supraspinatus (SS) and infraspinatus (IS) muscles from appropriate animals (n=6). The muscles from the injury side were compared to the muscles in the sham operated side of the same mouse. Data are represented as % loss of muscle weight after induced RC injury by comparing the injured to the sham operated muscles (*p<0.05; *p<0.001). FIGS. 5B and C show gene expression analysis of shoulder muscles (n=4). Gene expression was analyzed by qRT-PCR and normalized to the Rpl4 household gene. Data is shown as gene expression in injured compared to sham operated muscles for Cidec in FIG. 5B and for Lep in FIG. 5C**. Significance was determined by one-way ANOVA followed by post-hoc Tukey's tests. (*p<0.05).

DETAILED DESCRIPTION

I. Definitions

The following definitions refer to the various terms used above and throughout the disclosure.

The term "selective TGF-β inhibitor or antagonist" as used herein refers to a polypeptide that inhibits TGF-β1 and/or TGF-β3 signaling, but does not substantially inhibit TGF-β2 signaling.

Figure 1C:
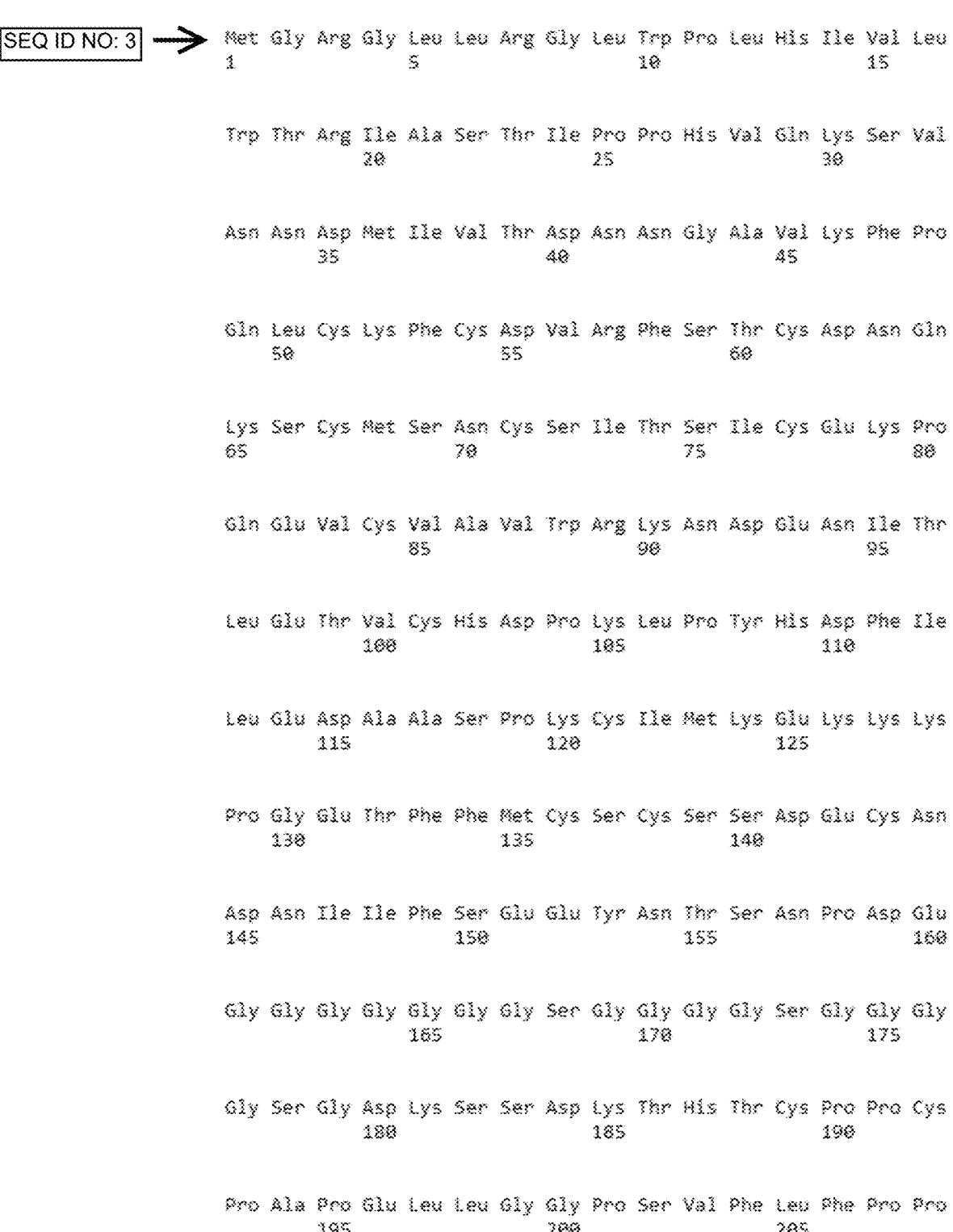
FIG. 1C is the amino acid sequence of a TGFβRII-Fc (SEQ ID NO:3) used in Examples 1-3 herein.

There are two splice-forms of TGFβRII, the native TGFβRII short-form (Uniprot SEQ ID P37173 which corresponds to SEQ ID NO:1 herein), and the native TGFβRII long-form (Uniprot SEQ ID D2JYI1 which corresponds to SEQ ID NO:2 herein). The long form is a splice variant with a 25 amino acid insertion after amino acid 31, where the amino acid flanking the insertion is changed from Val to Ile (FIG. 1).

As used herein a "TGFβRII ECD polypeptide fusion" comprises a polypeptide of the extracellular domain ("ECD") of TGFβRII and a heterologous sequence. The TGFβRII portion comprises a polypeptide sequence having at least 80%, or at least 85%, or at least 90%, or at least 95% sequence identity to the amino acid sequence set forth as amino acids 23 through 166 of SEQ ID NO:1; or at least 80%, or at least 85%, at least 90%, or at least 95% sequence identity to the amino acid sequence set forth as amino acids 23 through 191 of SEQ ID NO:2, and wherein the polypeptide is capable of binding TGF-β1 and/or TGF-β3, but does not substantially bind to TGF-132.

TGFβRII ECD polypeptide fusions include a polypeptide of TGFβRII, wherein TGFβRII comprises a polypeptide sequence beginning at any of positions 23 to 51 of SEQ ID NO:1 and ending at any of positions 143 to 166 of SEQ ID NO:1, or a sequence beginning at any of positions 23 to 76 of SEQ ID NO:2 and ending at any of positions 169 to 191 of SEQ ID NO:2, and wherein the polypeptide is capable of binding TGF-β1 and/or TGF-β3.

The heterologous sequence portion of a TGFβRII ECD polypeptide fusion can be a constant domain ("Fc") of a human IgG or albumin. When the TGFβRII portion is fused to the Fc of a human immunoglobulin, IgG, the resulting fusion protein is known as a "TGFβRII-Fc". In other words, a TGFβRII-Fc comprises or consists of the extracellular domain of the TGFβRII receptor, as described above, fused to the Fc of a human IgG. The human IgG moiety in a TGFβRII-Fc can consist of the Fc domain of human IgG1, IgG2, or IgG4. The TGFβRII portion can be fused with the Fc domain at the N-terminus or the C-terminus with a connecting linker of varying length and amino acid sequence, but preferably without secondary structure. A TGFβRII-Fc can comprise either the TGFβRII short-form or the long-form, and fusions containing either splice-form have similar binding specificities for TGF-β1 and/or TGF-β3; and they do not substantially bind TGF-β2.

Figure 2:
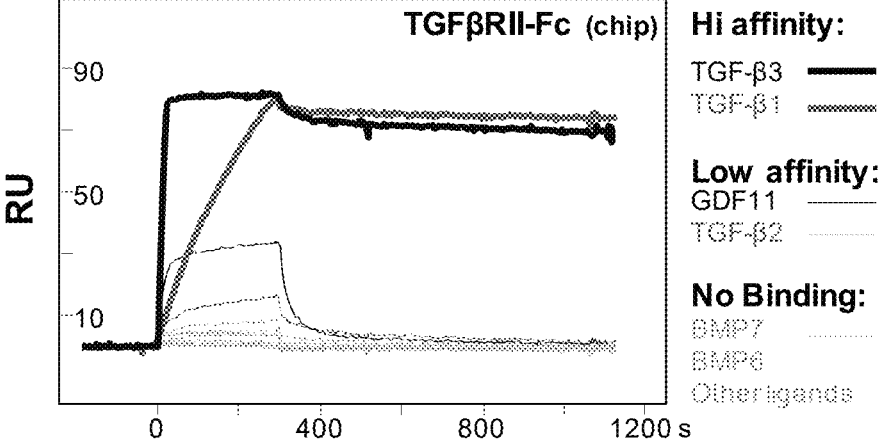
FIG. 2 shows the binding specificity of a TGFβRII-Fc. The figure is an image of an SPR-sensogram that shows binding of TGFβRII-Fc (SEQ ID NO:3) to TGF-β1 and TGF-β3, but not TGF-β2. See Aykul, S. and Martinez-Hackert, E. *Transforming Growth Factor-β family ligands can function as antagonists by competing for type II receptor binding.* Journal of Biological Chemistry 291: 10792-10804 (2016), which is hereby incorporated by reference in its entirety.

TGFβRII-Fc are known fusion proteins. For example, WO 1998/048024 reports a TGFβRII-Fc and methods of making a TGFβRII-Fc where the short form of TGFβRII is fused to the Fc of human IgG1. WO 1998/048024 is hereby incorporated by reference in its entirety. Additionally U.S. Pat. No. 9,809,637 reports a TGFβRII-Fc using the long form of TGFβRII. U.S. Pat. No. 9,809,637 is also hereby incorporated by reference in its entirety. TGFβRII-Fc is an inhibitor of TGF-β1 and/or TGF-β3. However, it does not substantially bind to/inhibit TGF-β2. See FIG. 2 which is taken from Aykul, S. and Martinez-Hackert, E. Transforming Growth Factor-0 family ligands can function as antagonists by competing for type II receptor binding. Journal of Biological Chemistry 291: 10792-10804 (2016), cited above. Without being bound by theory, it is a so-called "ligand trap," which works by trapping the ligands TGF-β1 and/or TGF-β3 in the intercellular compartment. This prevents the ligands from interacting with the endogenous TGFβRII receptor and, therefore, inhibits downstream signaling. Thus, a TGFβRII-Fc can be used as selective antagonists of TGF-β1 and/or TGF-β3, but substantially not TGF-β2.

In particular embodiments, TGFβRII-Fc has at least 80%, at least 85%, at least 90%, or at least 95% similarity to the amino acid sequence set forth as SEQ ID NO:3. See FIG. 1C. In further particular embodiments, the TGFβRII-Fc comprises or consists of the amino acid sequence set forth as SEQ ID NO:3.

The term "treat" and "treatment" refers to a method for reducing, inhibiting, or otherwise ameliorating FD by administering a therapeutically effective amount of a selective TGF-β inhibitor.

The term "fatty degeneration" ("FD") refers to the abnormal formation of fat tissue in between muscle fibers and the accompanying atrophy of muscles, which can be a result of injury or a disease/disorder.

The term "fatty infiltration" ("FI") refers to the abnormal formation of fat tissue only.

The term "administering" refers to both direct and indirect administration of a pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

The term "concomitant" or "concomitantly" includes administering an agent (e.g., selective TGF-β inhibitor) in the presence of a further agent. Concomitant administration in a therapeutic treatment method includes methods in which a first, second, third, or additional agents are co-administered. Concomitant administration also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may administer to the subject a second agent (e.g., selective TGF-β inhibitor), and the administering steps may be executed at the same time, or nearly the same time. The actor and the subject may be the same entity (e.g., human). Thus, the term embraces both simultaneous administration and substantially simultaneous administration, i.e., at about the same time.

The term "sequential administration" means not at the same time and means not almost at the same time. For example, one drug (active agent) may be taken at one time of day (e.g. in the morning) and the other taken at another time of day (e.g. in the evening/night time); or alternating days, etc. . . . . .

The term "effective amount" or "therapeutically effective amount" refers to the amount and/or dosage, and/or dosage regime of one or more agent(s) necessary to bring about the desired result e.g., an amount sufficient to prevent FD in a subject, an amount sufficient to reduce the occurrence of FD in a subject, and/or an amount sufficient to treat FD in a subject.

The terms "subject", "individual", and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments the subject may not be under the care or prescription of a physician or other health worker.

The term "surgery" or "surgical procedure" refers collectively to all therapeutic and diagnostic procedures, including procedures requiring an incision made on a subject as well as endoscopic procedures.

II. Pharmaceutical Compositions

In some embodiments, pharmaceutical compositions are provided comprising a selective TGF-β inhibitor, such as a TGFβRII-Fc, and a pharmaceutically-acceptable carrier. For example, a TGFβRII-Fc may be formulated with a pharmaceutically-acceptable carrier.

The compositions disclosed herein may be administered orally, parenterally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional, and intracranial injection or infusion techniques In a particular embodiment, the compositions are administered subcutaneously, intramuscularly or intravenously. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York), which is incorporated herein by reference in its entirety.

The compositions disclosed herein may be formulated for parenteral administration where the active ingredient may be incorporated into a solution or suspension or depot. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single subcutaneous dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound/complex in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the particular methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

U.S. Pat. Nos. 5,916,596, 6,506,405, and 6,537,579 teach the preparation of nanoparticles from the biocompatible polymers, such as albumin. Thus, provided herein are methods for the formation of nanoparticles by a solvent evaporation technique from an oil-in-water emulsion prepared under conditions of high shear forces (e.g., sonication, high pressure homogenization, or the like).

III. Methods of Use

It has been discovered that a selective TGF-β inhibitor, such as a TGFβRII-Fc, may be used to inhibit fibro-adipogenic progenitor cell (FAP) differentiation into adipocytes. The method comprises providing to the intercellular compartment surrounding a FAP cell an effective amount of a TGFβRII-Fc.

Any effective amount that inhibits differentiation into an adipocyte may be used, for example, 250 pM to about 2.5 mM, 100 µm to about 2.0 mM, or 50 µm to about 1.0 mM. In some embodiments, the effective amount is about 250 pM, about 500 pM, about 2.5 nM, about 5 nM, about 25 nM, about 50 nM, about 250 nM, about 500 nM, about 2.5 µM, about 5 µM, about 25 µM, about 50 µM, about 250 µM, about 500 µM, and about 2.5 mM.

Further, in one embodiment, the method can be performed in vitro. Additionally or alternatively, the method can be performed in vivo.

In further embodiments, it has now been discovered that a selective TGF-β inhibitor as defined herein, especially a TGFβRII-Fc, can be used to achieve a variety of desirable outcomes, and particularly to prevent, reverse, reduce the occurrence of, and/or treat FD.

Additionally or alternatively, the selective TGF-β inhibitor or a composition comprising the selective TGF-β inhibitor may be used to prevent, reverse, reduce the occurrence of, and/or treat muscle atrophy in a subject in need thereof which may or may not be separate from FD.

The selective TGF-β inhibitor may be administered or otherwise provided in a composition, such as a pharmaceutical composition further comprising one or more pharmaceutically acceptable excipients as described herein. Additional pharmaceutical therapeutic agents may also be administered concurrent or sequential with the selective TGF-β inhibitor.

In further embodiments, the therapeutically effective amount of the selective TGF-β inhibitor, is an amount that prevents, reverses, reduces the occurrence of, or treats FD. In one embodiment, the therapeutically effective amount of the selective TGF-β inhibitor ranges from about 50 µg to about 10 mg per kg of the subject, or 500 µg to about 3 mg per kg of the subject, or 500 µg to about 2 mg per kg of the subject, or 500 µg to about 1 mg per kg of the subject. In a further embodiment, the therapeutically effective amount of the selective TGF-β inhibitor, such as a TGFβRII-Fc, is about 0.5 mg to about 500 mg per dose, or about 1 mg to about 500 mg per dose, or about 5 mg to about 500 mg per dose, or about 10 mg to about 500 mg per dose, or about 10 mg to about 400 mg per dose, or about 20 mg to about 200 mg per dose, or about 20 mg to about 100 mg per dose, particularly about 50 mg per dose.

Alternatively, the selective TGF-β inhibitor can be administered at a dosage of about 0.01-100 mg/kg body weight, and more typically about 0.05-10.0 mg/kg body weight, or about 0.1-5.0 mg/kg body weight, or about 0.25-2.5 mg/kg body weight, or about 0.2-2 mg/kg body weight, or about 0.2-1.0 mg/kg body weight. Therefore, dosages for a single administration may typically be about 0.5-5,000 mg, or about 1-500 mg, or about 5-250 mg, or about 10-200 mg. Of course, dosages may also be adjusted within the above ranges according to one best tolerated by the individual.

The therapeutically effective amount of the selective TGF-β inhibitor, or a composition comprising the selective TGF-β inhibitor, may be administered one or more times depending on the identity and severity of the injury, surgery or condition. For example, the selective TGF-β inhibitor may be administered once per week, twice per week, three or more times per week, less than once per week, once every two weeks, once every three weeks, once every four or more weeks, semi-monthly, monthly, or bimonthly.

In some embodiments, the selective TGF-β inhibitor, or a composition comprising the selective TGF-β inhibitor, may be administered to a subject before, during, after surgery, or any combination thereof. For example, the selective TGF-β inhibitor may be administered to the subject at least about 1 minute before the surgical procedure begins, at least about 10 minutes before the surgical procedure begins, at least about 30 minutes before the surgical procedure begins, at least about 1 hour before the surgical procedure begins, at least about 3 hours before the surgical procedure begins, at least about 6 hours before the surgical procedure begins, at least about 12 hours before the surgical procedure begins, at least about 24 hours before the surgical procedure begins, at least about 48 hours before the surgical procedure begins, or more than 48 hours before the surgical procedure begins, for example one week, two weeks, 30 days, 60 days or 90 days before the surgical procedure begins; or from about 1 minute to about 24 hours before the surgical procedure begins, or about 1 minute to about 12 hours before the surgical procedure begins, or about 1 minute to about 1 hour before the surgical procedure begins. Additionally or alternatively, the selective TGF-β inhibitor, may be administered less than or equal to about 24 hours after the surgical procedure ends, less than or equal to about 12 hours after the surgical procedure ends, less than or equal to about 6 hours after the surgical procedure ends, less than or equal to about 3 hours after the surgical procedure ends, less than or equal to about 1 hour after the surgical procedure ends, less than or equal to about 30 minutes after the surgical procedure ends, less than or equal to about 10 minutes after the surgical procedure ends, less than or equal to about 1 minute after the surgical procedure ends; or from about 1 minute to about 24 hours after the surgical procedure ends, about 1 minute to about 12 hours after the surgical procedure ends, or about 1 minute to about 1 hour after the surgical procedure ends, or more than 48 hours after the surgical procedure ends, for example one week, two weeks, 30 days, 60 days or 90 days after the surgical procedure ends.

Additionally or alternatively, the selective TGF-β inhibitor may be administered 90 days, 60 days, 30 days, 25 days, 20 days, 15 days, 10 days or 5 days before or after surgery.

The surgery may be a repair surgery, such as a tendon, ligament and/or muscle repair surgery. For example, the repair surgery may be RC surgery, Achilles tendon surgery, Tendo-Achilles lengthening surgery, gastrocnemius recession surgery, anterior cruciate ligament (ACL) surgery, knee surgery, hip surgery, or spinal surgery. In a particular embodiment, the surgery is RC repair surgery.

Additionally or alternatively, the selective TGF-β inhibitor or a composition comprising the selective TGF-β inhibitor may be administered to a subject suffering from or at risk of suffering from osteoarthritis, such as hip and knee osteoarthritis, muscle atrophy, age-related sarcopenia, obesity, metabolic syndrome, diabetes, and/or a neuropathy, such as peripheral neuropathy.

Additionally or alternatively, the selective TGF-β inhibitor or a composition comprising the selective TGF-β inhibitor may also be administered to a subject suffering from or at risk of suffering from a neurodegenerative disease, such as amyotrophic lateral sclerosis; a neuromuscular disease, such as a muscular dystrophy and inclusion body myositis; or chronic obstructive pulmonary disease; or the subject may be a chronic non-ambulatory stroke patient.

Combination therapies are also provided herein. Thus, a selective TGF-β inhibitor, such as TGFβRII-Fc, and/or a pharmaceutical composition comprising a selective TGF-β inhibitor, and one or more other active agents may be used to prevent, reverse, reduce the occurrence of and/or treat FD. Further active agents for use with a selective TGF-β inhibitor include steroids for example. Further active agents may be administered concomitantly or sequentially as defined herein.

EXAMPLES

The following examples are provided to further illustrate the invention disclosed herein but, of course, should not be construed as in any way limiting its scope. In each example the TGFβRII-Fc used was the short form of TGFβR fused to human IgG1 (see SEQ ID NO:3).

Example 1—In Vivo Mechanism of Action; Inhibition of Adipogenic Differentiation Mechanistically, muscle infiltrating adipocytes are generated from muscle-resident fibro-adipogenic progenitor cells (FAPs) that are activated as part of the normal wound healing response. It was found that TGFβRII-Fc inhibits adipocyte differentiation from a FAPs-like cell-line, i.e., 3T3-L1 cells (see FIGS. 3A-3H). This supports the idea that TGFβRII-Fc works by preventing FAPs differentiation into adipocytes in vivo.

Cryopreserved murine 3T3-L1 pre-adipocytes, purchased from ZenBio, were thawed and seeded at approximately 10,000 cells/cm$^2$ in Preadipocyte Medium (PM: DMEM, high glucose, HEPES pH 7.4, 10% Bovine Calf Serum (BCS), and Penicillin+Streptomycin (PS)). Cells were maintained at 37° C. in a humidified incubator with 5% CO$_2$ until reaching 100% confluence, which takes in about four days. During this time, growth media was replaced every other day. Two days after reaching confluence, Preadipocyte Medium (PM) was replaced with an appropriate volume of Differentiation Medium (DM: DMEM, high glucose, sodium pyruvate, HEPES pH 7.4, 10% Fetal Bovine Serum (FBS), 33 µM Biotin, 10 µg/ml Human insulin, 1 µM Dexamethasone, 0.5 mM 3-Isobutyl-1-methylxanthine (IBMX)) and incubated for 3 days. Differentiation Medium was then replaced with Adipocyte Maintenance Medium (MM: DMEM high glucose, sodium pyruvate, HEPES pH 7.4, 10% FBS, 33 µM Biotin, 10 µg/ml Human insulin). Cells were maintained up to 10 days post-differentiation with medium exchange every other day.

In this assay 3T3-L1 cells were treated with TGFβRII-Fc beginning at different stages of differentiation. In one assay, confluent 3T3-L1cells were grown in PM, differentiated 3 days in DM and maintained up to 5 days in MM. 300 nM of TGFβRII-Fc was added at day 0 (beginning of DM treatment), or at day 3 (end of DM treatment), or at day 5 (after 2 days in MM). Cells were kept under treatment until the end of the experiment at day 8 or day 10.

At the end of the experiment adipocyte differentiation was measured by immunofluorescence. In this experiment, 10,000 3T3-L1 cells/cm$^2$ were plated in a 96-well plate in preadipocyte media. At day 0, cells were treated with TGFβRII-Fc. Treatments were continued in the appropriate medium to allow adipocyte differentiation until day 10. At day 10, cells were washed twice with PBS and fixed with 10% formalin for 30 min at RT. Cells were then washed twice with PBS, followed by staining with 0.01% saponin, 1 µg/ml Nile Red and 1 µg/ml DAPI in PBS for 15 min at RT. After staining, cells were washed 3 times with PBS. Images were taken with an Olympus Fluoview FC1000 confocal laser scanning microscope.

Figures 3A, 3B, 3C, 3D, 3E, 3F, 3G:
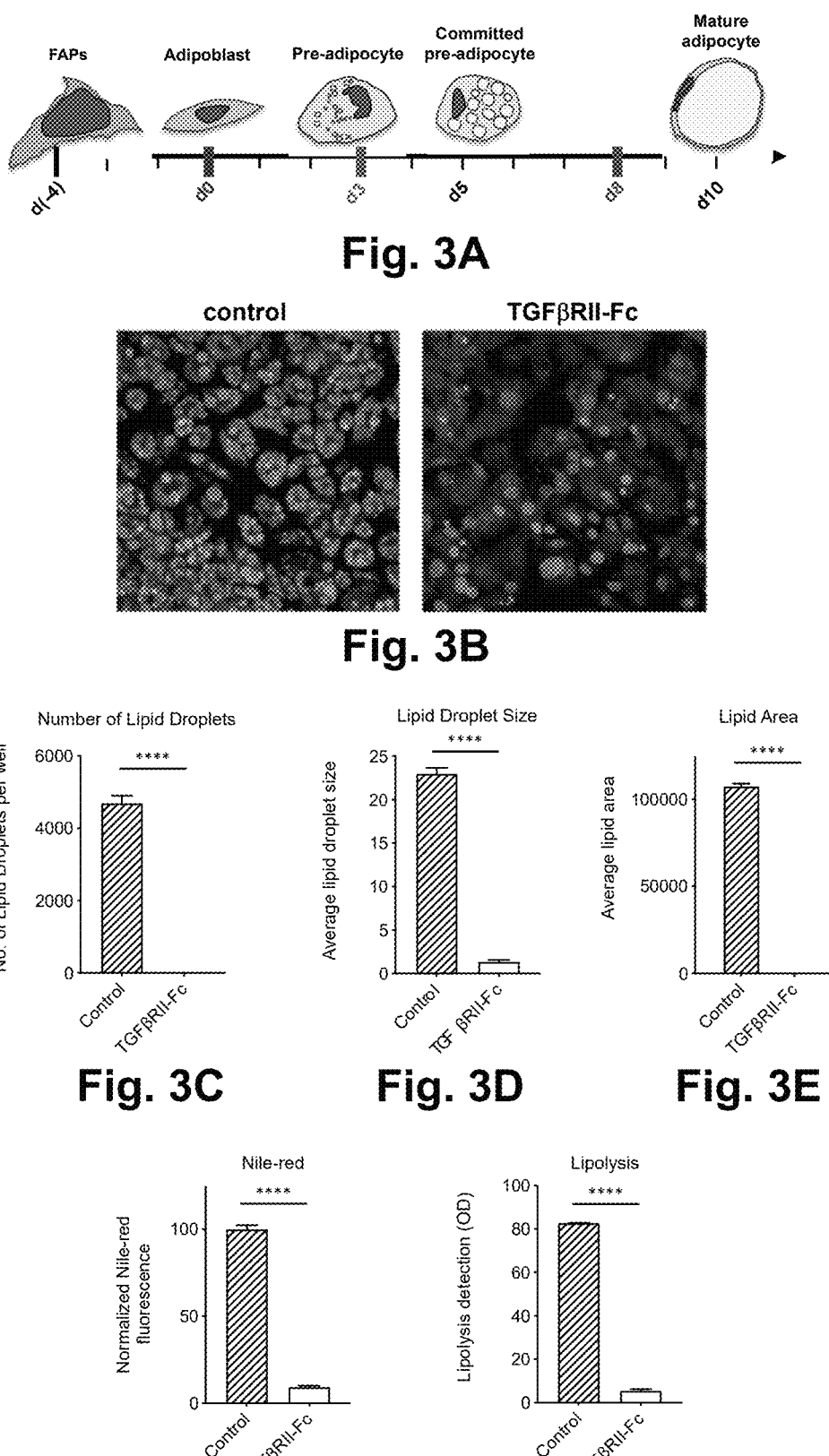
FIGS. 3A-3M show inhibition of differentiation of fibro-adipogenic 3T3-L1 progenitor cells into adipocytes by a TGFβRII-Fc.
Figures 3H, 3I, 3J, 3K, 3L, 3M:
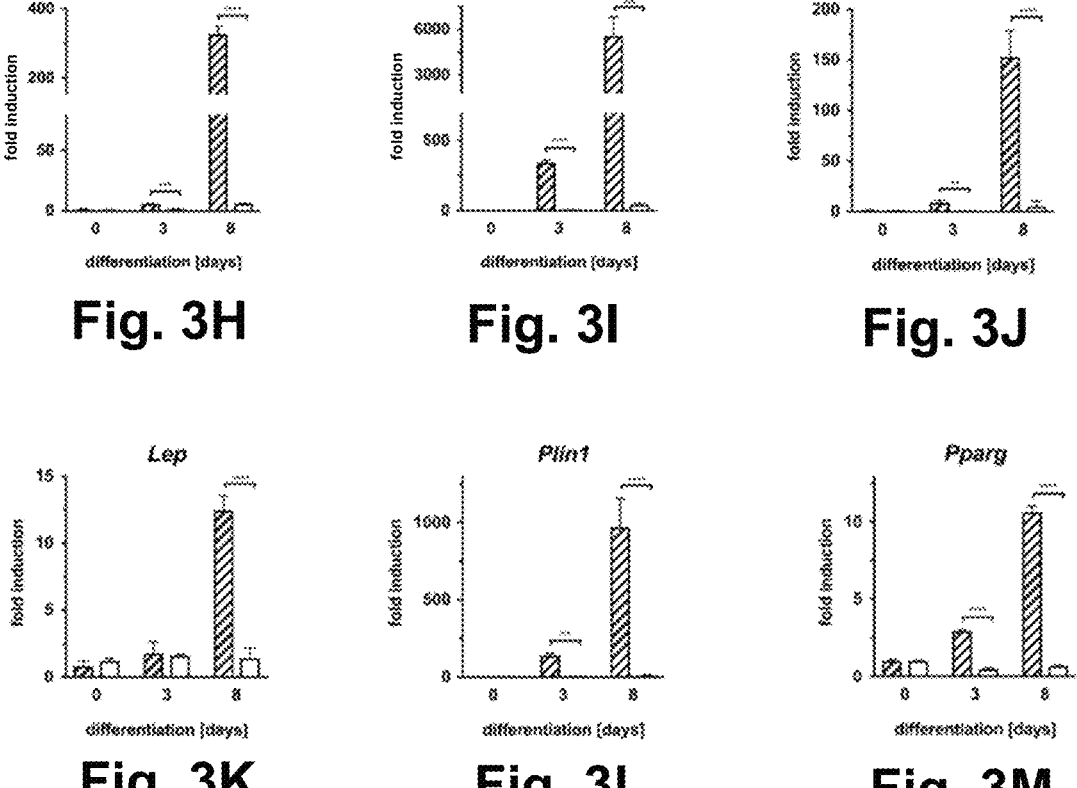

Results from this experiment are shown in FIGS. 3A-3M. 3T3-L1 cells were treated with a TGFβRII-Fc or vehicle (i.e., PBS) on day 0, and differentiated for 8 days (FIG. 3A). The number of new adipocytes was reduced by 95% (FIGS. 3B-3G). In FIG. 3B green represents Nile Red staining of lipid droplets and purple represents DAPI staining of nuclei. For quantitative Nile Red and DAPI fluorescence measurements, fluorescence is measured before and after staining according to published protocols. In this experiment 3T3-L1 cells were treated in quadruplicates in a 96 well plate. Multiple images were taken from each well. Number and size of lipid droplets, the average lipid area, normalized Nile-red fluorescence and lipolysis activity were calculated using Image J software from two biological replicates (FIGS. 3C-3M).

In such an adipocyte differentiation experiment the extent of adipocyte formation can also be determined by gene expression analysis. In the experiment resulting in the data obtained in FIGS. 3C-3H, 3T3-L1 cells were treated with TGFβRII-Fc or vehicle on day 0 and differentiated for 8 days. Total RNA was isolated from 3T3-L1 cells at day 0, day 3 and day 8, and cDNA was synthesized from RNA by reverse transcriptase using published protocols. To quantify expression of a selection of adipocyte marker genes primer pairs amplifying specific regions in these genes were synthesized and cDNA was analyzed by a Lightcycler 480 (Roche). For each experiment primer standard curves were created using a dilution series, spanning 4 orders of magnitude, from genomic DNA isolated from 3T3-L1 cells according to published protocols. The highest concentration of genomic DNA yields qRT-PCR amplification at around cycle 20 for the majority of primer pairs. A Tm-curve is also performed as a quality control for each primer pair at the end of each qRT-PCR run to verify that only a single amplicon is produced by each primer pair and that no primer dimers are formed. Data are usually obtained from at least two biological replicates and four technical replicates.

Example 2—Mouse Diet-Induced Obesity (DIO) Model

TGFβRII-Fc inhibits FI of skeletal muscles in a mouse DIO model, as shown in FIGS. 4A-4J. In this model, mice are placed on a high fat diet (HFD) for several weeks. After 4 weeks on HFD mice show early signs of developing obesity. One of these signs is an increase of FI of skeletal muscles. FI is the first manifestation of FD in DIO, with muscle atrophy developing later. New fat cells are generated by adipogenic differentiation of fibro-adipogenic progenitor cells (FAPs) that reside in the muscle and can be detected by histopathologic and gene expression analyses.

In this experiment a total of 20 8-week old, male C57BL/6 mice, obtained from Charles River Laboratories, were used. Animals were housed under supervision of the Michigan State University (MSU) Campus Animal Resources and allowed to acclimate for seven days prior to the start of the study. Upon arrival all animals were provided with PMI Nutrition International Certified Rodent Chow No. 5CR4. At the beginning of the experiment 14 mice were placed on a high fat diet, (Research Diet D12492, 60% fat kcal). This diet was provided ad libitum throughout the remainder of the study. Regular chow (PMI Nutrition International Certified Rodent Chow No. 5CR4) was provided ad libitum to 6 control mice throughout the study. Mice on high fat diet were separated into two groups and 7 mice were treated with TGFβRII-Fc and 7 with vehicle (i.e., PBS) for 4 weeks. Dosing with TGFβRII-Fc or vehicle control was done by bi-weekly subcutaneous injections. TGFβRII-Fc was provided as a stock of 3 mg/ml and dosed at 15 mg/kg body weight. TGFβRII-Fc aliquots were kept frozen (−80° C.) until used. On the day of dosing, an aliquot was moved from −80° C. to the bench at room temperature at least one hour before dosing. Thawed samples were gently mixed by inverting the tube to ensure homogeneous distribution followed by centrifugation to collect the liquid from the cap. Vortexing or harsh mixing methods were avoided to prevent protein denaturation or bubble formation. Vehicle control was given to appropriate animals at the same time as TGFβRII-Fc. The experiment was performed under supervision of the IACUC of MSU to ensure animal safety. At the end of the experiment mice were sacrificed by $CO_2$ asphyxiation. At necropsy leg muscles were extracted and flash frozen in liquid nitrogen.

FI of skeletal muscles can be determined in such an experiment by histopathologic analysis of muscles. For this analysis muscles can be frozen in liquid nitrogen and then fixed in paraformaldehyde followed by cryoprotection with sucrose. Cryosections of the muscles can then be stained for hematoxylin and Oil Red 0 (ORO). In this assay ORO detects intermuscular and intramuscular fat. Intermuscular fat is the result of FI, while intramuscular fat is a result of lipid accumulation within muscle fibers. In the DIO model accumulation of both intermuscular and intramuscular fat can be detected.

Figures 4A, 4B, 4C, 4D, 4E, 4F, 4G, 4H, 4I, 4J:
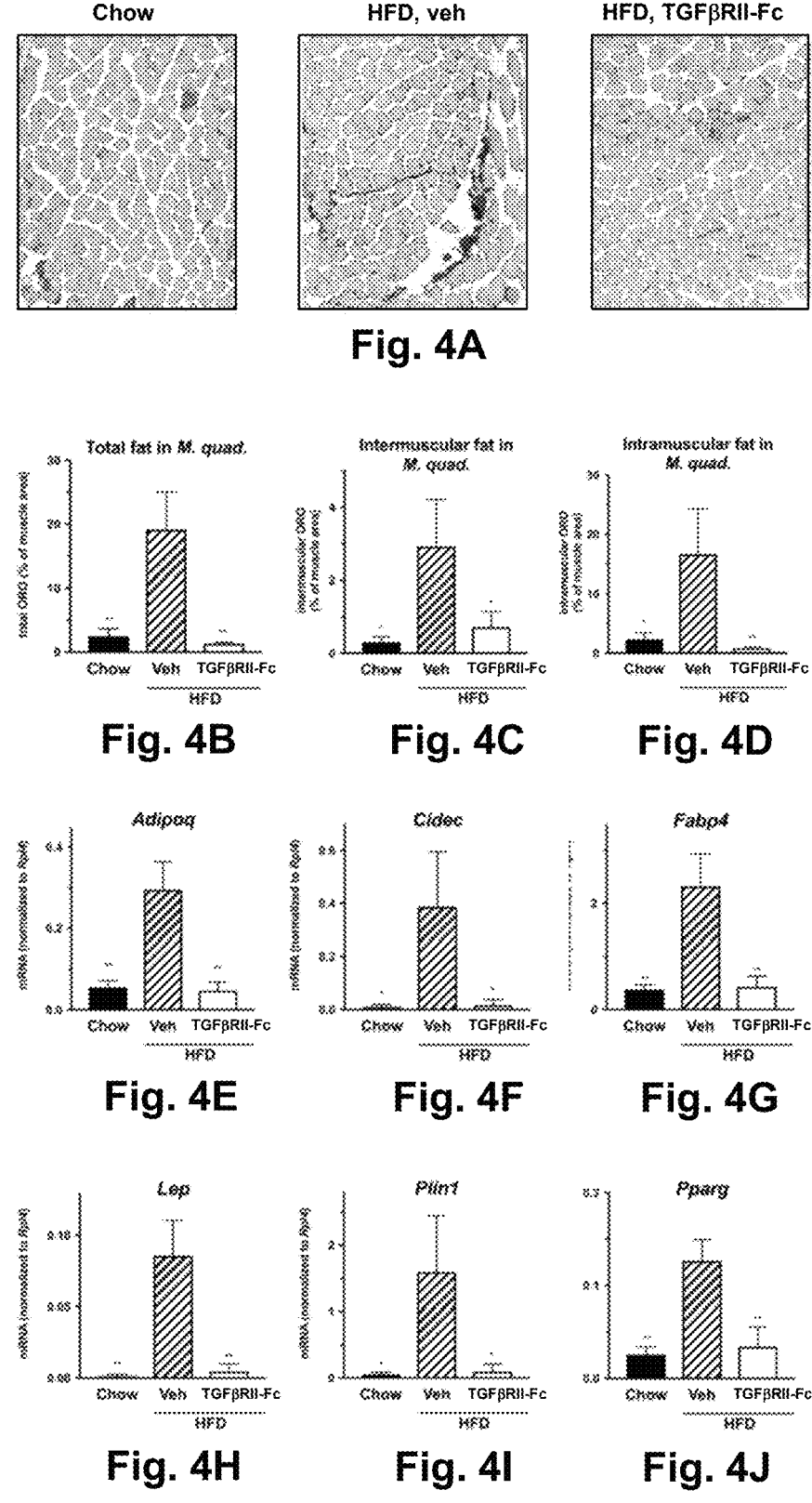
FIGS. 4A-4J show inhibition of fatty infiltration ("FI") in the *Musculus* quadriceps femoris of DIO mice by a TGFβRII-Fc.

In this experiment, shown in FIG. 4A, quadriceps muscles of mice fed a HFD for 4 weeks and treated with TGFβRII-Fc or vehicle control were analyzed by histopathology. Quadriceps muscles were placed into a 15 ml tube with 8 ml of 4% paraformaldehyde in phosphate buffer solution (no saline) and kept for 48 h at RT. Muscles were then transferred to fresh 15 ml tubes with 8 ml of 30% sucrose in phosphate buffer solution (no saline) and kept at 4° C. until the muscles sank to the bottom of the tube (i.e., 4 days). Fixed and sucrose cryoprotected muscles were then embedded in OCT and cryosectioned at 12 μm at −20° C. Sections were stained with ORO and counterstained with hematoxylin. Quantification of ORO was done using Image J on images obtained with an OlyVIA system at 0.7× magnification. Inhibition of FI by a TGFβRII-Fc under these conditions was evidenced by a 70-80% reduction in total ORO staining as well as a 65-70% reduction in intermuscular ORO (FIG. 4A-4D).

In this type of an experiment, FI of skeletal muscles can also be determined by gene expression analysis. RNA was isolated from a portion of the belly of the appropriate muscle (20-25 mg) using the ReliaPrep™ RNA tissue miniprep system from Promega and a tissue homogenizer. Tissue was placed into a 2 ml screw cap tube and two beads and 1.3 ml TRIzol™ Reagent was added. Tissue is homogenized 2× for 4 minutes using a mixer mill (Retsch) at a frequency of 25 $s^{-1}$. Samples were placed on ice in between cycles. 260 μl chloroform was added and the samples shaken vigorously by hand until the solution was a cloudy pink color. After centrifugation at 4° C. for 10' at 15k×g an aliquot of 750 μl of the aqueous phase was transferred to a new tube, avoiding the interphase. 340 μl of ice-cold isopropanol was added, and the sample was mixed by vortexing. The sample was then transferred onto a Promega RNA Cell Miniprep column and processed according to the manufacturer's instructions. A DNAse 1 treatment step was performed on the column for 30 min. RNA was eluted in 15 μl RNase-free $H_2O$. The RNA concentration and the purity of each sample were determined by Nanodrop. For cDNA synthesis 1 μg of total isolated RNA was used from each sample and reverse transcribed using the Multiscribe™ Reverse Transcriptase enzyme kit (from ThermoFischer). cDNA was then analyzed as previously described using primers for adipocyte markers on a Roche Lightcycler® 480. Data was then normalized to a household gene (Rpl4).

In this experiment gene expression was analyzed in the quadriceps muscles of mice that had been on a HFD for 4 weeks and treated with TGFβRII-Fc or vehicle control. Treatment with TGFβRII-Fc significantly inhibited FI under these conditions, as evidenced by 5 to 60-fold reduction in expression of the adipocyte marker genes Adipoq, Cidec, Fabp4, Lep, Plin1 and Pparg (FIG. 4E-4J).

Surprisingly, it was found that inhibition of both TGF-β1 and β3 prevents adipogenesis, as shown in FIGS. 3A-3H and FIGS. 4A-4J, a counterintuitive result considering previous reports that TGF-β1 itself inhibits adipogenesis by Ignotz, R. A. and Massague, J. Proc Natl Acad Sci USA. 1985 December; 82(24):8530-4. doi: 10.1073/pnas.82.24.8530.). Further, because TGFβRII-Fc does not inhibit TGF-β2 signaling, the administration of TGFβRII-Fc before, during and/or after, for example, RC repair surgery may inhibit, prevent or reduce the occurrence of FD of muscles without interfering with tendon regeneration. Thus, TGFβRII-Fc may also facilitate tendon regeneration and attachment while inhibiting FD. TGFβRII-Fc can also be used to halt FD of muscles in patients, where RC repair surgery is not recommended and conservative treatment is indicated.

Example 3—Inhibition of Fatty Degeneration of Skeletal Muscles in a Mouse Model of Rotator Cuff Injury In this experiment the tendons of two RC muscles, the supraspinatus and the infraspinatus muscles, are resected to approximate the RC tendon tears found in human patients. This mouse model of RC injury is a good mimic for RC injuries in humans, since mice also develop significant FD including FI and muscle atrophy in the shoulder muscles after 6 weeks, as well as fibrosis/scarring.

In this experiment surgery to induce RC injury was done by RC tendon transection and denervation. Surgical procedures were performed under general anesthesia with 2.5% isoflurane and oxygen. The surgical interventions in the RC were performed in the right shoulder of the mice, and a sham surgery was performed in the left shoulder. For surgery mice were placed on a surgical table, and the clavicle bone and the deltoid muscle were exposed through a skin incision. The trapezius muscle was separated to expose the suprascapular nerve, and a segment of the nerve 5 mm long was resected to prevent the reattachment and healing of the nerve. The deltoid muscle was longitudinally split to expose the rotator cuff tendons at the shoulder joint. The supraspinatus and infraspinatus tendons were completely transected with removal of the tendon portion to decrease the chance of incidental healing. The deltoid and trapezius muscles and skin incision were closed. For the sham procedure on the contralateral shoulder, the skin and muscle incisions were performed, the rotator cuff and/or suprascapular nerve identified, and the muscle and skin closed again. Surgery typically last approximately 20 min per mouse.

In this experiment surgery to induce RC injury was performed on 24 female 12-week old C57BL/6 mice obtained from Jackson Laboratories. Starting two days after surgery 12 mice were treated with TGFβRII-Fc, and 12 mice were treated with vehicle control (i.e., PBS) for 6 weeks. The study was performed at the MSU InVivo Facility under supervision of MSU's IACUC to ensure animal safety.

At the beginning of the experiment animals were housed under supervision of the MSU Campus Animal Resources. Animals were allowed to acclimate for seven days prior to the start of the study. Upon arrival, PMI Nutrition International Certified Rodent Chow No. 5CR4 was provided and given to the animals ad libitum for the duration of the study. On the day before the study the animals were weighed and randomized into two treatment groups in such a way as to generate cohorts with no significant difference between them with respect to their body weights. Animals were singly housed for the study after cohorts were generated. Mortality/moribundity checks were performed twice daily, once in the morning and once in the evening, for two days after surgery and once daily for all subsequent days of the study. Post-operative care included cleansing of the surgery incisions with chlorhexidine solution daily for two days after surgery. Animals were assessed daily post operatively for use of limb and weighed daily to assess feed intake. For post-operative pain management 1 mg/kg buprenorphine was injected subcutaneously every 12 hours for two days following surgery.

In this experiment TGFβRII-Fc or vehicle was administered bi-weekly to animals starting two days after surgery for 6 weeks. TGFβRII-Fc or vehicle was administered by subcutaneous route. TGFβRII-Fc was provided as a stock of 3 mg/mL and dosed at 15 mg/kg body weight. TGFβRII-Fc aliquots were kept frozen (−80° C.) until used. On the day of dosing, an aliquot was moved from −80° C. to the bench at room temperature at least one hour before dosing. Thawed samples were gently mixed by inverting the tube to ensure homogeneous distribution followed by centrifugation to collect the liquid from the cap. Vortexing or harsh mixing methods were avoided to prevent protein denaturation or bubble formation. Vehicle control (i.e., PBS) was given to appropriate animals at the same time as TGFβRII-Fc treatment.

At the end of the experiment animals were sacrificed by $CO_2$ asphyxiation. At necropsy the shoulder girdle and upper limbs were excised en block with the muscles and connective tissues. The supraspinatus and infraspinatus muscles from the injured and sham operated sides were separated from bones and connective tissues and immediately weighed. Wet weights were recorded and the weight of the operated muscle was calculated as a percentage of the sham operated control muscle. Statistical significance of differences between muscle weights from TGFβRII-Fc and vehicle treated animals was determined by a Student's t-test (n=6).

Figure 5A:
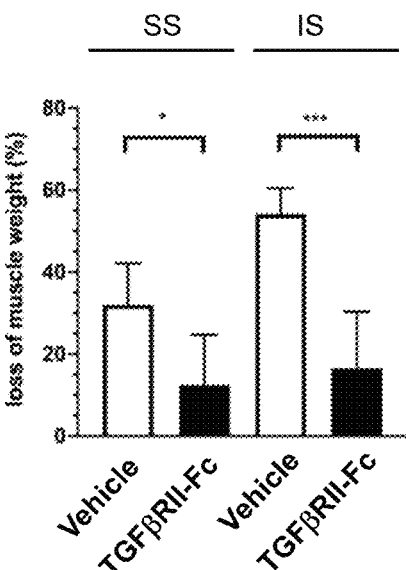
FIGS. 5A-5C show inhibition of muscle atrophy and FI in shoulder muscles after induced RC injury by a TGFβRII-Fc.

In this experiment treatment TGFβRII-Fc significantly reduced atrophy of the supraspinatus (SS) and infraspinatus (IS) muscles after RC injury (see Table 1 and FIG. 5A). Vehicle treated animals lost on average about 30% of their SS muscle weight and about 55% of their IS muscle weight. In contrast, muscles from animals treated with TGFβRII-Fc lost only around 10% and 13% of their SS and IS muscle weight respectively. This corresponds to a 70-80% reduction of muscle atrophy in mice treated with TGFβRII-Fc compared to control mice.

TABLE 1

| Shoulder Muscle Weights at Tissue Harvest | | | | | |
|---|---|---|---|---|---|
| Group No. | Animal No. | muscle | left side (g)[a] | right side (g)[b] | % loss of muscle weight[c] |
| 1 | 1004 | supraspinatus | 0.0414 | 0.0337 | 18.6 |
| 1 | 1005 | supraspinatus | 0.0288 | 0.0212 | 26.4 |
| 1 | 1006 | supraspinatus | 0.0389 | 0.0213 | 45.2 |
| 1 | 1010 | supraspinatus | 0.0257 | 0.0153 | 40.5 |
| 1 | 1011 | supraspinatus | 0.0268 | 0.0173 | 35.4 |
| 1 | 1012 | supraspinatus | 0.0327 | 0.0242 | 26.0 |
| 2 | 2004 | supraspinatus | 0.0296 | 0.0237 | 19.9 |
| 2 | 2005 | supraspinatus | 0.0310 | 0.0233 | 24.8 |
| 2 | 2006 | supraspinatus | 0.0242 | 0.0288 | −19.0 [d] |
| 2 | 2010 | supraspinatus | 0.0312 | 0.0313 | −0.3 [d] |
| 2 | 2011 | supraspinatus | 0.0346 | 0.0333 | 3.8 |
| 2 | 2012 | supraspinatus | 0.0388 | 0.0289 | 25.5 |
| 1 | 1004 | infraspinatus | 0.0433 | 0.0176 | 59.4 |
| 1 | 1005 | infraspinatus | 0.0265 | 0.0136 | 48.7 |
| 1 | 1006 | infraspinatus | 0.0303 | 0.0144 | 52.5 |
| 1 | 1010 | infraspinatus | 0.0351 | 0.0127 | 63.8 |
| 1 | 1011 | infraspinatus | 0.0319 | 0.0168 | 47.3 |
| 1 | 1012 | infraspinatus | 0.0218 | 0.0102 | 53.2 |
| 2 | 2004 | infraspinatus | 0.0231 | 0.0158 | 31.6 |
| 2 | 2005 | infraspinatus | 0.0198 | 0.0178 | 10.1 |
| 2 | 2006 | infraspinatus | 0.0219 | 0.0159 | 27.4 |
| 2 | 2010 | infraspinatus | 0.0270 | 0.0325 | −20.4 [d] |
| 2 | 2011 | infraspinatus | 0.0303 | 0.0293 | 3.3 |
| 2 | 2012 | infraspinatus | 0.0292 | 0.0213 | 27.1 |

Figure 5B:
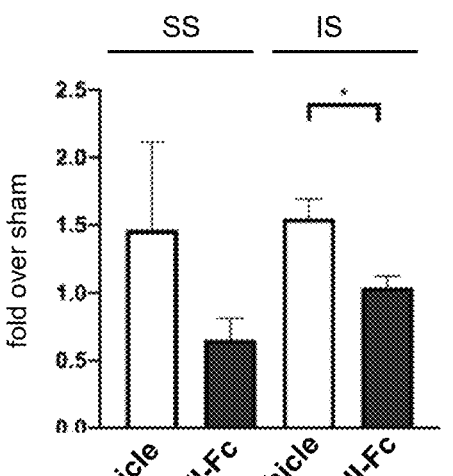
Figure 5C:
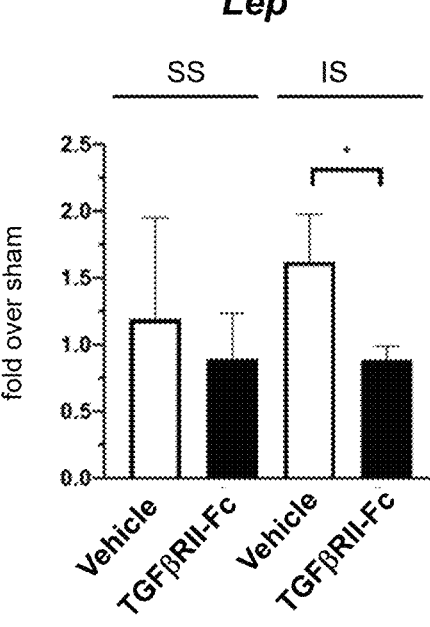

[a]Sham surgery
[b]Induced RC Injury surgery
[c]% loss of right side compared to left side
[d] negative number means a gain in weight in right side compared to left side Reduction of FI in shoulder muscles after RC injury by TGFβRII-Fc, can also be shown using adipocyte marker gene expression analysis. In this experiment the SS and IS muscles from the injured and sham operated sides were flash frozen in liquid nitrogen. RNA was isolated from an entire muscle using the ReliaPrep™ RNA tissue miniprep system from Promega and a tissue homogenizer, followed by cDNA synthesis as described. Treatment with TGFβRII-Fc reduced FI in the SS and infraspinatus IS muscles, as shown by 2-3 fold reduction in Cidec and Lep gene expression (FIGS. 5B and 5C). Significance was determined by a Student's t-test (n=4).

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Particular embodiments of this invention are described herein, including the best mode known to the inventors for carrying out the invention. Variations of those particular embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. A method for reducing the occurrence of and/or treating fatty degeneration of skeletal muscle in a subject in need thereof, the method comprising administering a therapeutically effective amount of a TGFβRII-Fc to the subject;

wherein the TGFβRII-Fc is administered to the subject immediately before surgery to 90 days before surgery, during surgery, and/or immediately after surgery to 90 days after surgery; and wherein the surgery is a repair surgery selected from the group consisting of rotator cuff (RC) surgery, Achilles tendon surgery, Tendo-Achilles lengthening surgery, gastrocnemius recession surgery, anterior cruciate ligament (ACL) surgery, knee surgery, hip surgery, and spinal surgery; and wherein the TGFβRII-Fc has at least 90% sequence identity to SEQ ID NO: 3.

2. The method of claim 1, wherein the TGFβRII-Fc inhibits fatty degeneration while also facilitating tendon regeneration.

3. The method of claim 1, wherein the subject has or is at risk of having osteoarthritis, muscle atrophy, age-related sarcopenia, obesity, metabolic syndrome, diabetes, and/or a peripheral neuropathy.

4. The method of claim 1, wherein the subject has a neurodegenerative disease, a neuromuscular disease, a chronic obstructive pulmonary disease, or the subject is a chronic non-ambulatory stroke patient.

5. The method of claim 1, wherein the TGFβRII-Fc is administered at least once per week, once every two weeks, or once every three weeks.

6. The method of claim 1, wherein the therapeutically effective amount of the TGFβRII-Fc is about 10 mg to about 500 mg per dose.

7. The method of claim 6, wherein the therapeutically effective amount of the TGFβRII-Fc is about 20 mg to about 100 mg per dose.

8. The method of claim 1, wherein the TGFβRII-Fc is administered subcutaneously, intramuscularly, or intravenously.

9. The method of claim 1, wherein the subject is human.

10. The method of claim 1, wherein the subject is a non-human mammal.

11. A method for reducing the occurrence of and/or treating fatty degeneration of skeletal muscle in a subject in need thereof, the method comprising administering a therapeutically effective amount of a TGFβRII-Fc to the subject, wherein the subject has or is at risk of having osteoarthritis, muscle atrophy, age-related sarcopenia, obesity, metabolic syndrome, diabetes, or a peripheral neuropathy; and wherein the TGFβRII-Fc has at least 90% sequence identity to SEQ ID NO: 3.

12. The method of claim 11, wherein the TGFβRII-Fc inhibits fatty degeneration while also facilitating tendon regeneration.

13. The method of claim 11, wherein the TGFβRII-Fc is administered at least once per week, once every two weeks, once every three weeks, once a month, once every two months, once every three months, once every six months, or once every 12 months.

14. The method of claim 11, wherein the therapeutically effective amount of the TGFβRII-Fc is about 10 mg to about 500 mg per dose.

15. The method of claim 14, wherein the therapeutically effective amount of the TGFβRII-Fc is about 20 mg to about 100 mg per dose.

16. The method of claim 11, wherein the TGFβRII-Fc is administered subcutaneously, intramuscularly, or intravenously.

17. A method for reducing the occurrence of and/or treating fatty degeneration of skeletal muscle in a subject in need thereof, the method comprising administering a therapeutically effective amount of a TGFβRII-Fc to the subject, wherein the subject has a neurodegenerative disease, a neuromuscular disease, a chronic obstructive pulmonary disease, or the subject is a chronic non-ambulatory stroke patient; and wherein the TGFβRII-Fc has at least 90% sequence identity to SEQ ID NO: 3.

18. The method of claim 17, wherein the TGFβRII-Fc inhibits fatty degeneration while also facilitating tendon regeneration.

19. The method of claim 17, wherein the TGFβRII-Fc is administered at least once per week, once every two weeks, once every three weeks, once a month, once every two months, once every three months, once every six months, or once every 12 months.

20. The method of claim 17, wherein the therapeutically effective amount of the TGFβRII-Fc is about 10 mg to about 500 mg per dose.

21. The method of claim 20, wherein the therapeutically effective amount of the TGFβRII-Fc is about 20 mg to about 100 mg per dose.

22. The method of claim 17, wherein the TGFβRII-Fc is administered subcutaneously, intramuscularly, or intravenously.

* * * * *